United States Patent [19]

Stroud

[11] 4,423,277
[45] Dec. 27, 1983

[54] ALKYLATION PROCESS UTILIZING ABSORPTION REFRIGERATION

[76] Inventor: William R. Stroud, 10537 Beinhorn, Houston, Tex. 77024

[21] Appl. No.: 392,418

[22] Filed: Jun. 25, 1982

[51] Int. Cl.$^3$ .................................................. C07C 2/56
[52] U.S. Cl. .................................. 585/719; 585/718; 585/723; 585/730
[58] Field of Search ......................... 585/718, 719, 723

[56] References Cited

U.S. PATENT DOCUMENTS

| | | | |
|---|---|---|---|
| Re. 26,060 | 7/1966 | Nathan | 585/719 |
| 2,425,745 | 8/1947 | Leonard et al. | 585/718 |
| 2,988,580 | 6/1961 | Smith et al. | 585/719 |
| 3,082,274 | 3/1963 | Mayer | 585/719 |
| 3,105,102 | 9/1963 | Webb, Jr. | 260/683.58 |
| 3,673,271 | 6/1972 | Golasby | 585/718 |
| 3,925,501 | 12/1975 | Putney et al. | 585/719 |
| 4,041,101 | 8/1977 | Sobel | 585/718 |
| 4,128,597 | 12/1978 | Jones | 260/683.62 |
| 4,130,593 | 12/1978 | Jones | 260/683.48 |
| 4,144,281 | 3/1979 | Chapman et al. | 585/719 |
| 4,214,114 | 7/1980 | Carson | 585/715 |
| 4,218,575 | 8/1980 | Webb, Jr. | 585/715 |
| 4,293,729 | 10/1981 | Kolb et al. | 585/715 |

FOREIGN PATENT DOCUMENTS

671352 10/1963 Canada ............................ 585/719

Primary Examiner—Delbert E. Gantz
Assistant Examiner—Cynthia A. Prezlock
Attorney, Agent, or Firm—Fulbright & Jaworski

[57] ABSTRACT

A method for utilizing low level or waste heat in a petroleum refinery through absorption refrigeration of isoparaffinic hydrocarbons, e.g., isobutane. In an alkylation process, an olefin is contacted with a molar excess of isoparaffinic hydrocarbons to produce an alkylate. A portion of unreacted isoparaffinic hydrocarbons is vaporized to provide refrigeration. They are cooled and condensed by contact with a lean oil absorbent. They are recovered from the absorbent by use of low level heat in a distillation step and returned to the reaction zone.

44 Claims, 6 Drawing Figures

FIG. 1
TIME - TANK REACTOR SYSTEM

MODIFIED SYSTEM

CONVENTIONAL SYSTEM

FIG. 2
CASCADE REACTOR SYSTEM

FIG. 3

EFFLUENT REFRIGERATION SYSTEM

MODIFIED SYSTEM

CONVENTIONAL SYSTEM

ALKYLATION PROCESS UTILIZING ABSORPTION REFRIGERATION

PRIOR ART STATEMENT

The following is a listing which in the opinion of the applicant sets forth the closest prior art of which the applicant is aware. A concise explanation of the relevance of each listed item is included.

1. Alkylation is a conventional technique used extensively in the petroleum refining industry. More specifically, olefins are reacted with an isoparaffinic hydrocarbon such as isobutane to form a branched chain, paraffinic hydrocarbon with high antiknock qualities. This product, called alkylate, is the basis for aviation and high octane gasoline.

2. U.S. Pat. No. 3,105,102, Webb, Sept. 24, 1963, and 4,218,575, Webb, Aug. 19, 1980, disclose conventional processes for alkylating isoparaffinic hydrocarbons with olefinic hydrocarbons in the presence of an acid catalyst and an excess of isoparaffinic hydrocarbons. Unreacted isobutane is recovered by fractionation and is recycled to the reactor to serve both as a reactant (in excess) and as a refrigerant. These patents will be referred to frequently herein as representing current art.

3. U.S. Pat. No. 4,214,114, Carson, July 22, 1980, is directed to an acid-catalyzed alkylation process wherein an isoparaffinic hydrocarbon is reacted with an olefinic hydrocarbon in a reaction zone. Unreacted isoparaffinic and normal paraffinic hydrocarbons are vaporized from the liquid reaction mixture to provide evaporative cooling, and the resultant vapors are separated in a separation zone in open communication with the reaction zone.

4. U.S. Pat. No. 4,293,729, Kolb, et al., Oct. 6, 1981, discloses a conventional alkylation process wherein an olefin is reacted with an excess of isobutane in the presence of a sulfuric acid catalyst to produce a liquid hydrocarbon effluent containing alkylate product and a vaporous hydrocarbon effluent containing predominantly isobutane. Residual acid in the liquid hydrocarbon effluent is neutralized, and the liquid portion is then distilled to remove isobutane as a distillate and liquid alkylate as bottoms. Residual water in the vaporous overhead fraction is removed by means such as an acid scrubbing step. Thereafter, the vaporous isobutane distillate is combined with the vaporous hydrocarbon effluent from the reactor for compression and recycle to the reactor.

5. U.S. Pat. No. 4,128,597, Jones, Dec. 5, 1978, teaches a process for catalytic alkylation of isobutane with an olefin to produce an alkylate in a liquid reactor effluent stream. The liquid stream also includes isobutane which is partially vaporized to provide refrigeration for condensers in the alkylation process. The isobutane vapors are then compressed to provide heat for distillation in the process.

6. U.S. Pat. No. 4,130,593, Jones, Dec. 19, 1978, is similar in its disclosure to U.S. Pat. No. 4,128,597. The former patent teaches the use of a vapor system wherein, after isobutane vapors from the reactor effluent are compressed, the vapors are condensed and one or more columns are employed to remove inert alkanes, such as propanes, from the isobutane. The isobutane stream is then sent to a vapor-liquid separator, and the liquid isobutane stream is returned to the reactor for further reaction and for cooling purposes.

BACKGROUND AND SUMMARY OF THE INVENTION

Alkylation is a process whereby an isoparaffinic hydrocarbon such as isobutane is reacted with an olefin (such as propylene, butylene and/or pentene) to form a high octane hydrocarbon stream known as alkylate that boils in the gasoline boiling range of from about 100° to about 430° F. There are two primary catalysts typically employed to promote this reaction, hydrofluoric acid (HF) and sulfuric acid.

The HF alkylation process operates at essentially atmospheric temperature (about 80° to about 120° F.) and ordinarily does not require a refrigeration system. However, in some instances, it may be feasible to operate the process at lower temperatures as would require refrigeration.

The sulfuric acid alkylation process is used in numerous refineries and operates in the range of from about 35° to about 60° F., and more specifically in the 40° to 50° F. range, to prevent the formation of undesirable products. Thus, refrigeration is necessary in order to chill the inlet streams and to remove exothermic heat of reaction.

At least four types of reactor systems typically are employed in commercial alkylation facilities, including the time-tank, the cascade, the effluent refrigeration, and the closed cycle refrigeration system utilizing the effluent refrigeration system reactor. Each of these will be described later herein.

In almost every instance, the reaction temperature is maintained at 40° F. to 50° F. by employing a system utilizing the vapor compression refrigeration cycle. Major components include: evaporation, compression, condensation, and recycle of refrigerant. In the closed cycle systems such as time-tank and the closed cycle effluent reactor, ammonia or propane is used predominantly as the refrigerant. In the open systems, isobutane vapors created by the process are the refrigerant. These vapors are predominantly isobutane, but include equilibrium concentrations of ethane, propane, normal butane, pentanes, and minor quantities of heavier hydrocarbons vaporized from the reaction mixture.

Because process conditions vary so greatly from unit to unit and between geographic areas, one cannot generalize on the energy requirements to produce a given quantity of alkylate product. However, by way of example, a conventional effluent refrigeration unit designed to produce 8,000 B/D of alkylate may require a 5500 to 6000 horsepower refrigerant compressor.

Obviously, substantial energy in the form of electricity or high pressure steam, etc. is necessary to carry out compression as described above. The present invention is directed to a method whereby these energy costs may be reduced substantially, resulting in significant economic benefit. By using sources of heat in a refinery that might otherwise be lost to air and water from streams being cooled, for example, below about 300° F., this "waste" heat is used in the present invention to create refrigeration for the alkylation unit through the use of absorption refrigeration. Sources of low (temperature) level heat that may be employed in the system of the present invention include low pressure steam, furnace stacks, hot liquid and vapor streams, and the like. While the system of the present invention may dispense with the use of a compressor in an alkylation refrigeration system, the preferred embodiment herein contemplates the use of a compressor but reducing the compression ratio from the typical 5 to 8:1.0 level to about 2.0 to 2.5:1.0 with consequent substantial reduction in refrigeration expense.

It is, therefore, an object of the present invention to provide an improved alkylation process whereby vaporous excess and unreacted isoparaffinic hydrocarbons from the reactor are cooled and condensed for recycle to the reactor by means of absorption refrigeration.

Another object of the present invention is to provide such an improved alkylation process whereby cooling and condensing of the vaporous unreacted isoparaffinic hydrocarbons may be effected by either direct or indirect heat exchange in the absorption refrigeration step.

A still further object of the present invention is to provide an improvement in the catalytic alkylation of an isoparaffinic hydrocarbon such as isobutane with an olefin wherein the olefin is contacted with a molar excess of isobutane in the presence of a catalyst in a reactor, the reactor effluent including at least alkylate and isobutane. From the reactor effluent is separated a substantially liquid stream containing alkylate and isobutane and a substantially vaporous stream containing predominantly isobutane. Systems presently utilizing closed cycle refrigeration systems will be converted to this type refrigeration. The substantially vaporous stream is admixed with an absorbent and condensed to substantially a liquid followed by distillation of the condensed liquid whereby isobutane vapor is separated as distillate from the absorbent. The isobutane distillate is returned to the reactor to maintain an excess of the isoparaffinic hydrocarbon and for cooling purposes.

Yet another object of the present invention is the provision of such an improved alkylation process wherein, prior to admixing the substantially vaporous stream from the reactor with the absorbent, the stream is compressed to a higher pressure.

Still other objects, features and advantages of the present invention will be apparent from the following description of the preferred embodiments of the invention, given for the purpose of disclosure and taken in conjunction with the accompanying drawings.

DEFINITIONS

In the Detailed Description of the Preferred Embodiment, Alternative Embodiments and Claims sections, several terms will be used repeatedly. To avoid repetitive clarifying statements, the following definitions will apply to the terms as used later herein.

Bauxite Treating refers to a process whereby a liquid hydrocarbon stream is pumped through a bed of activated bauxite or alumina whereby contaminants such as water, sulfur oxides, sulfuric and sulfurous acids, esters and other sulfur compounds are removed by absorption and reaction with the solid.

Caustic Treating refers to a process whereby dilute concentrations of sodium hydroxide in water are mixed with hydrocarbon streams to remove contaminants such as sulfur oxides, sulfurous and sulfuric acids, esters and other sulfur compounds. The caustic may be separated from the hydrocarbon by electrostatic precipitation or settling followed by a water wash of the hydrocarbons.

Economizers refer to various devices which create isobutane vapors at intermediate pressures between the suction pressure and the discharge of the compressor. They may consist of simply a flash drum or a heat exchanger which permits vapor/liquid separation (kettle reboiler). The isobutane vapors created are fed to intermediate compression stages of a multi-stage compressor. Compression horsepower is reduced in this manner since the vapors bypass the initial stages of compression. In the present invention, economizers can be utilized to bypass the compressor completely.

Isobutane or Isobutane Vapors refer to those hydrocarbons created by vaporizing the reaction mixture. The vapor will be predominantly isobutane, but will contain equilibrium quantities of ethane, propane, normal butane, pentanes, and minor quantities of heavier hydrocarbons vaporized from the mixture.

Isoparaffinic Hydrocarbons refers to hydrocarbons other than alkylate. It will be predominantly isobutane, but will contain significant quantities of ethane, propane, normal butane, pentanes and minor quantities of alkylate.

Lean Oil or Absorbent refers to the bottoms product stream from the rectifier. It will contain equilibrium concentrations of propane, isobutane, normal butane, pentanes, and heavier hydrocarbons. The heavier hydrocarbons are injected into the system initially and are either added to or subtracted from depending upon losses from the system. These heavier hydrocarbons can be any non-olefin hydrocarbon or mixtures thereof boiling in the 150°–430° F. range which are compatible with the alkylation process. Typical sources include alkylate, heavy alkylate (produced by fractionating total alkylate into a light and heavy component), virgin naphtha, raffinates, and/or solvents. Other similar streams normally found within a petroleum refinery may be suitable.

Figure 5:
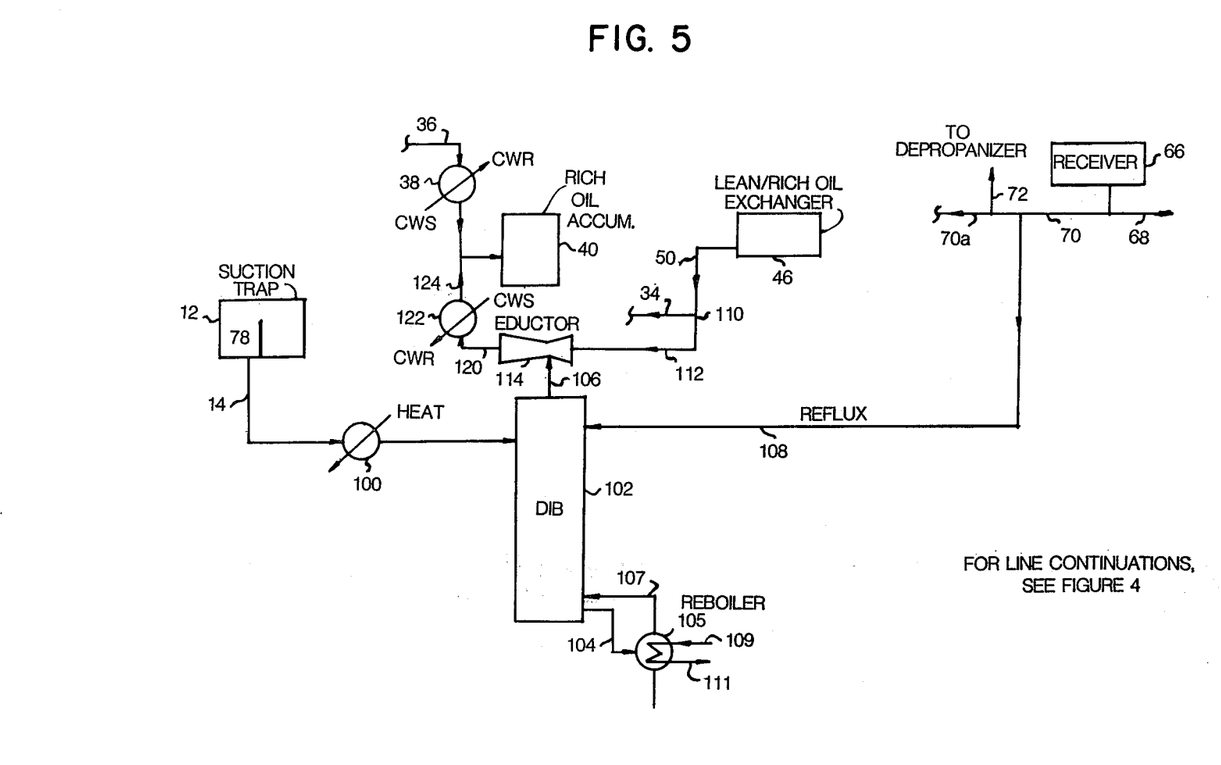
FIG. 5 is a schematic flow diagram similar to that of FIG. 4 with the added provision of a schematic illustration of a method for processing the alkylate in association with the absorption refrigeration system of the present invention.
Figure 6:
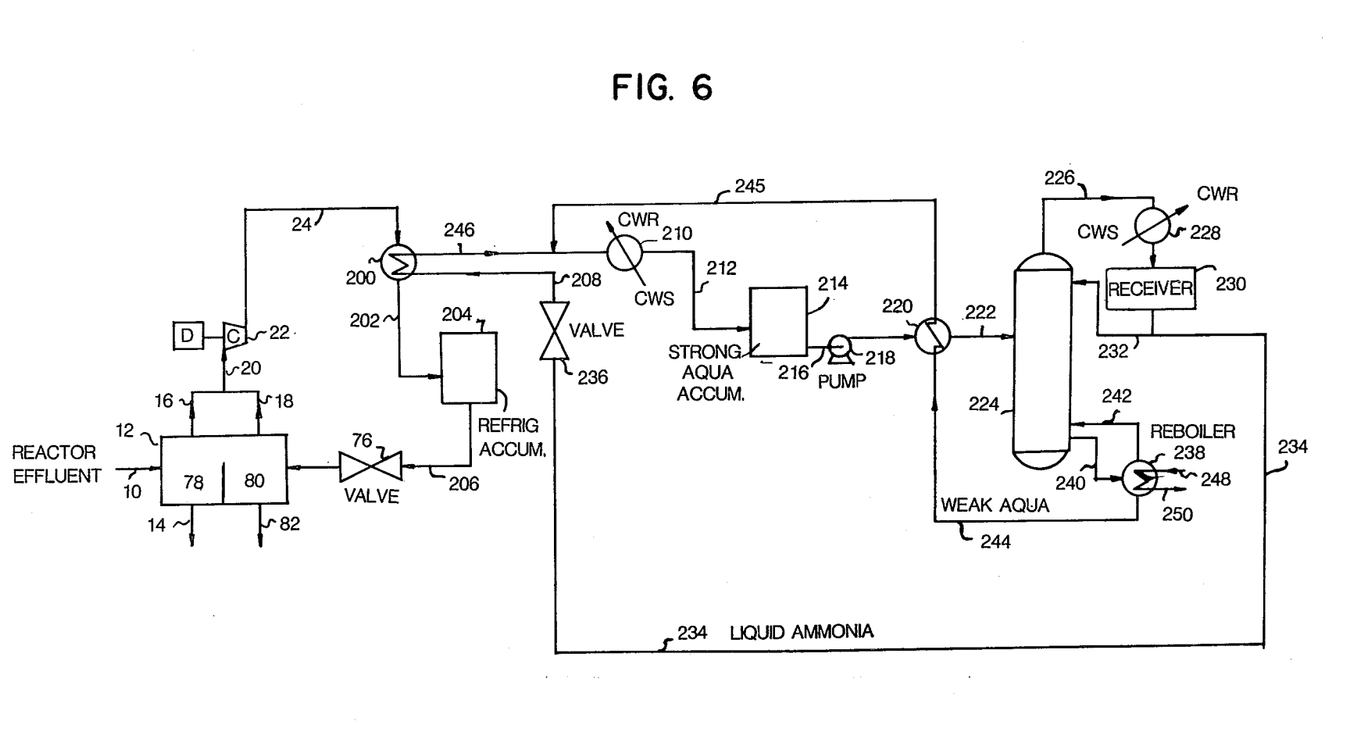
FIG. 6 is a schematic flow diagram of a further embodiment of an absorption refrigeration system in a sulfuric acid alkylation process according to the present invention.

Reboilers in FIGS. 5, 6 and 7 are shown schematically as if they were kettle-type-once-through reboilers. However, reboiler configuration and bottoms product withdrawal methods may be any conventional system known to those skilled in the art of distillation. Multiple reboilers may be used in some instances to take advantage of waste heat at lower temperature levels.

Rectifier refers to any conventional distillation process which separates hydrocarbons by boiling.

Waste Heat refers to any heat energy presently being lost to air or water because there is no economically attractive way to utilize this heat within the refinery area. If the low pressure steam system cannot be used to collect and deliver this heat to the rectifier reboiler, a separate system might be required to recover and deliver waste heat from various sources in other refinery areas. This might consist of a circulating hot water or hot oil system.

DETAILED DESCRIPTION OF THE PREFERRED EMBODIMENT

It is understood that there are at least four different reactor systems employed commercially for purposes of contacting a molar excess of isoparaffinic hydrocarbons with an olefin in the presence of an acid catalyst to produce an alkylate. The isoparaffinic hydrocarbon in conventional alkylation processes typically comprises isobutane (iC$_4$). The olefins typically include, for example, propylene (C$_3$=), butylenes (C$_4$=) and/or pentenes (C$_5$=).

When isobutane vapors are created by vaporizing a portion of the reaction mixture, said vapors will contain minor quantities of water, sulfur oxides, sulfurous and sulfuric acid, esters, and other sulfur compounds. If these contaminants are not removed, severe corrosion will occur at the elevated temperatures incurred in the present invention.

Figure 1:
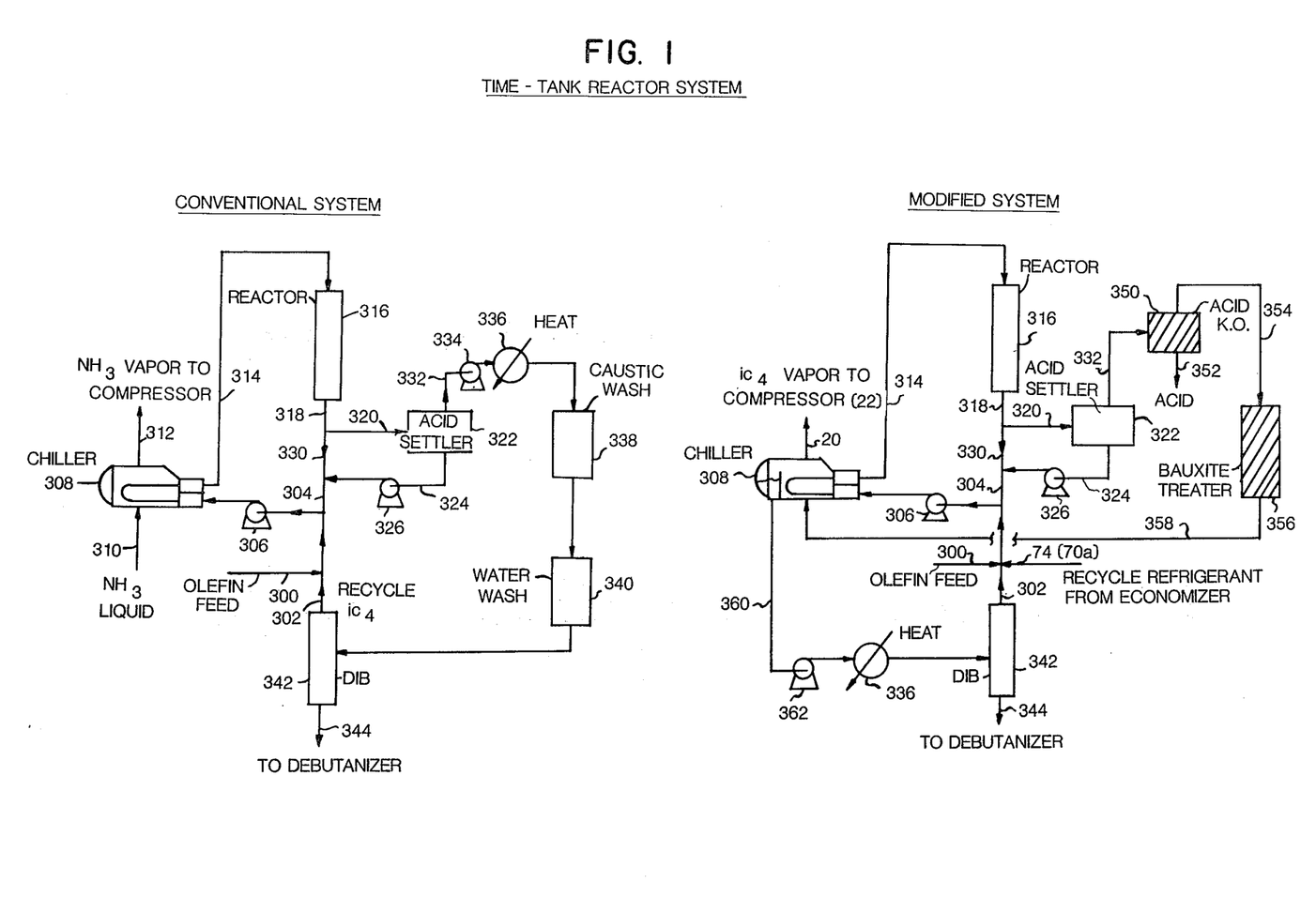
FIG. 1 is a schematic flow diagram showing both the conventional time-tank reactor system and the modifications required to employ the present invention.
Figure 2:
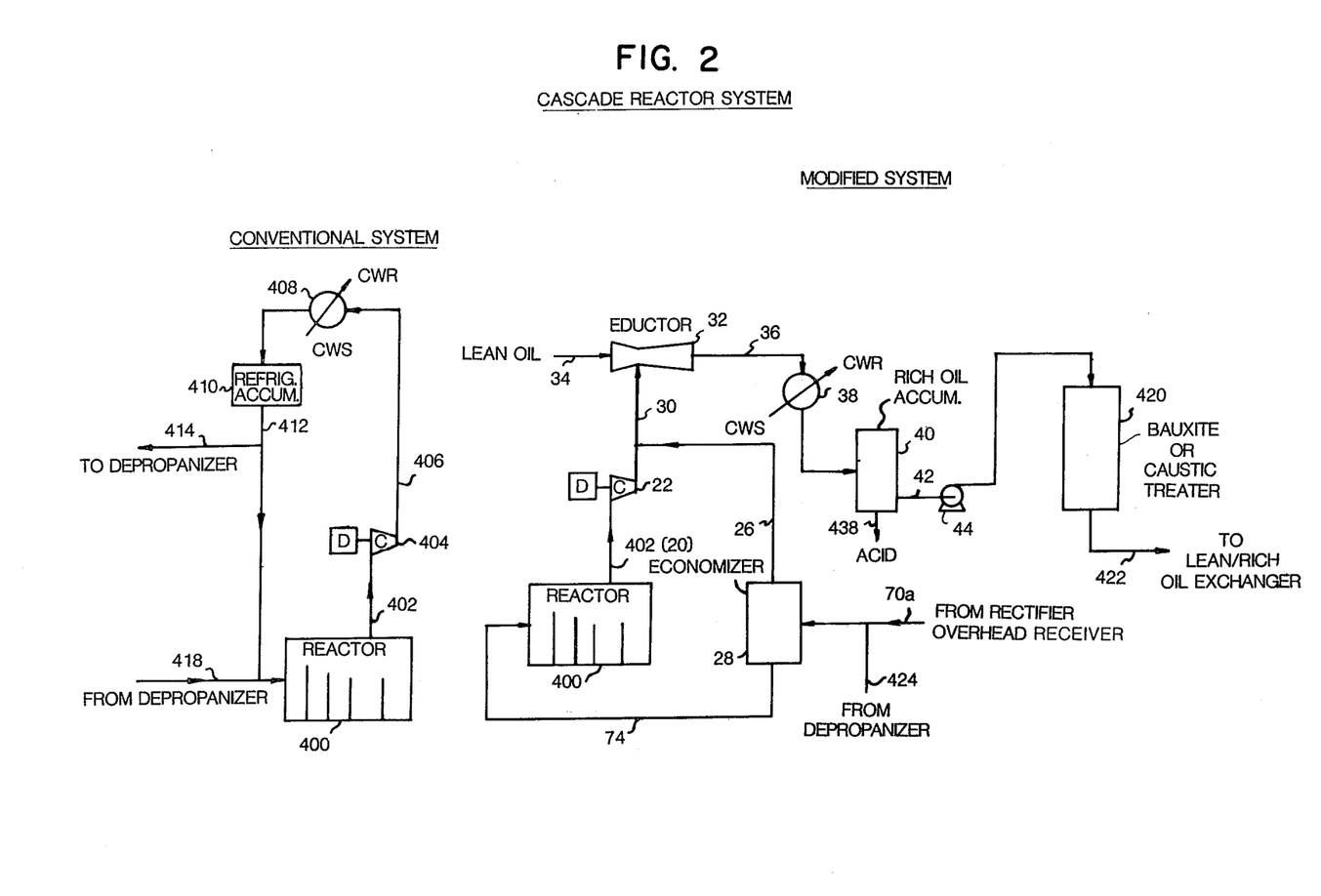
FIG. 2 is a schematic flow diagram showing both the conventional cascade reactor system and the modifications required to employ the present invention.
Figure 3:
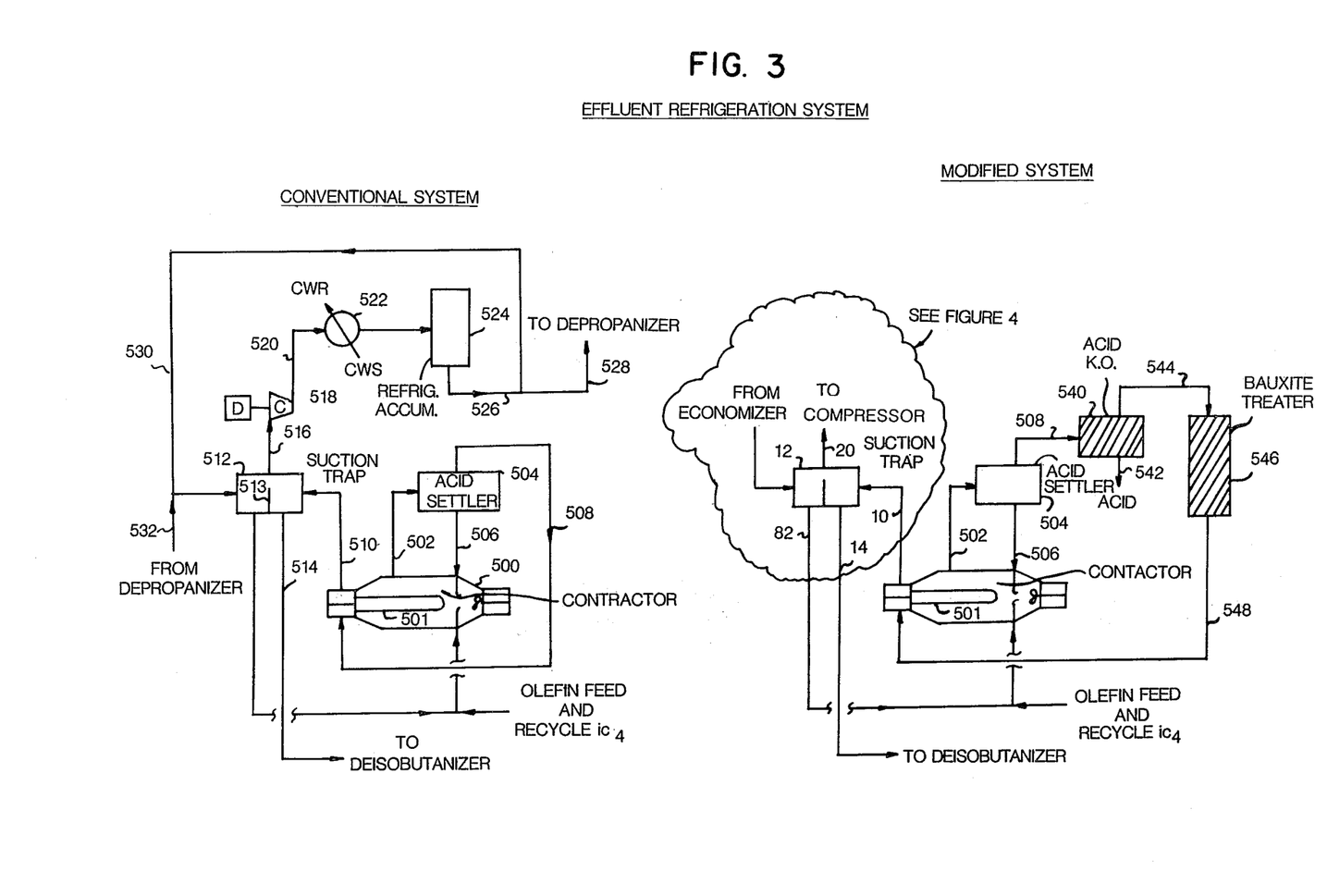
FIG. 3 is schematic flow diagram showing both the conventional effluent reactor system and the modifications required to employ the present invention.
Figure 4:
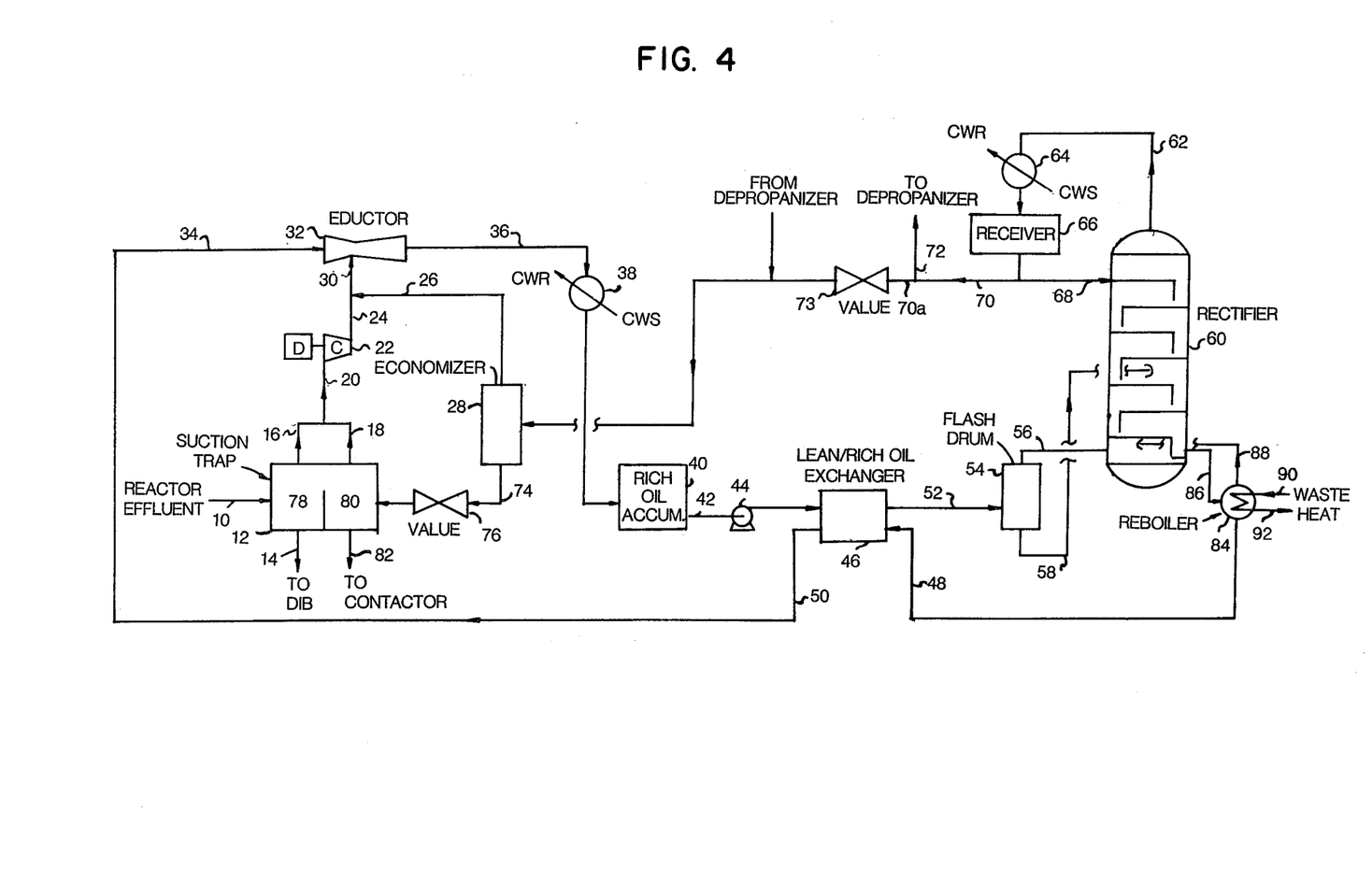
FIG. 4 is a schematic flow diagram of an absorption refrigeration system providing cooling for a sulfuric acid alkylation process according to the present invention.

FIGS. 1 through 3 show schematically the conventional reactor systems on the left side of the drawing. The modifications required (according to the present invention) to remove the contaminants and to create isobutane vapors in systems presently using closed refrigeration cycles are shown on the right side of each drawing. The processing of the isobutane vapor created in each system is illustrated in FIGS. 4, 5 and 6. It is understood that these figures illustrate the general process sequences and that many specific variations may exist commercially. Only those pieces of equipment affected by the present invention are shown.

TIME-TANK

The time-tank reactor system is illustrated in FIG. 1. The time-tank was one of the original reactor systems employed, but relatively few units remain in service today. In this system, the time-tank reactor 316, chiller 308, circulation pump 306, and connecting pipeline comprise the reactor system. Rapid circulation of an emulsion of acid, alkylate, and isoparaffinic hydrocarbons through this external loop serves to (1) dilute the olefin, (2) remove the heat of reaction in the chiller, and (3) contact isobutane with the catalyst. Olefin feed 300 is mixed with recycle and makeup isobutane 302 and injected into the circulating emulsion 304. This mixture is pumped by pump 306 to chiller 308 where the heat of reaction is removed by indirect cooling. Typically, ammonia liquid 310 (or propane or other refrigerant) is fed to the chiller 308 where it is vaporized into stream 312, creating refrigeration. The cooled emulsion 314 flows to the time-tank 316 where sufficient residence time exists for the reaction to take place. A continuous slip stream 320 of the circulating emulsion 318 is withdrawn and sent to the settler 322. This is a horizontal vessel with sufficient holding time to permit complete separation of the liquid hydrocarbon stream 332 containing alkylate and isoparaffinic hydrocarbons from the acid 324. Settled acid 324 is returned to the emulsion stream 330 by pump 326. Liquid hydrocarbon stream 332 is pumped by pump 334 and heated to about 80°–160° F. in exchanger 336 before flowing through caustic wash 338 and water wash 340 to the deisobutanizer (DIB) tower 342. The caustic wash removes sulfur compounds contained in the effluent hydrocarbon stream, and the water wash removes caustic that may be carried over the caustic wash. In the DIB tower 342, recycle isobutane 302 is recovered as an overhead product and the bottoms stream 344 will flow to storage as alkylate product or to a debutanizer for further process.

In the present invention (as illustrated in FIG. 1 as the "Modified System"), the effluent hydrocarbon stream 332 from the acid settler 322 will flow to a new acid knockout drum 350. Here any excessive carryovers which might occur from settler 322 will be allowed to settle to protect the treater. Recovered acid 352 will be returned to the system. Essentially acid-free effluent hydrocarbon steam 354 will flow to a bauxite treater 356 where contaminants will be removed by adsorption and reaction with the activated bauxite clay or alumina. Contaminant-free hydrocarbon 358 flows to chiller 308 where it replaces ammonia liquid 310 as the refrigerant. An isobutane vapor stream 20 (FIG. 4) is created by reducing the pressure in the chiller and by the transfer of the heat of reaction. It flows to the compressor 22 as illustrated in FIG. 4 to be discussed hereinafter. Unvaporized reactor effluent 360 is removed from the chiller and is pumped by pump 362 through heat exchanger 336 to the DIB 342. Caustic wash 338 and water wash 340 probably can be bypassed since the bauxite treater 356 should have removed the contaminants. Isobutane vapors 20 reovered as shown in FIG. 4 will return to the circulating emulsion 304 from the economizer 28 as stream 74. In some isolated instances it may be economical to return stream 70a from the overhead receiver 66 instead of stream 74.

Conversion of the conventional system to the present invention results in at least two advantages in addition to the savings in compression horsepower. The yield and quality (measured by octane number) of the alkylate product is improved as the isobutane concentration in the reaction zone increases. In conventional systems, isobutane concentration is a function of the recycle rate and purity of the DIB overhead and the benefits of improved alkylate quality and yield must be balanced against the investment and operating costs required by the deisobutanizer. In the present invention, the heat of reaction removed in the chiller is used to vaporize isobutane, with said isobutane vapor being returned to the circulating emulsion, resulting in a significantly higher concentration of isobutane in the reaction mixture than is normally the case. Thus a yield and quality improvement credit can be claimed. Second, concentration is increased to such an extent that the recycle rate from the DIB may be reduced. This saves utility consumption in the DIB and creates spare capacity in the DIB system.

CASCADE REACTOR

The cascade reactor system is illustrated and described in detail in U.S. Pat. No. 4,218,575, Webb, Aug. 19, 1980, in FIG. 1 and Column 3, line 58, titled "FIG. 1 Structure and Function". Therefore, FIG. 2 and this section will address only those areas impacted upon by the present invention.

In conventional cascade reactor systems, the reactor 400 in FIG. 2 (10 in Webb) is an auto-refrigerated reactor-settler combination. All of the reactants, olefins, isoparaffinic hydrocarbons, and acid are mixed and reacted in this vessel. As the exothermic heat of reaction is released, isobutane vapors 402 are created. These vapors flow to compressor 404 where pressure is increased to 100-120 psia; i.e., a compression ratio of 5-8:1. The compressor discharge 406 is cooled and condensed to, for example, 100° F. in heat exchanger 408 and then flows to the refrigerant accumulator 410. A portion of the refrigerant condensate 412 is sent to a depropanizer as stream 414 to purge propane from the system. The balance 416 returns to reactor 400 where it is mixed with the returning depropanizer bottoms 418. In some larger installations, economizers may be used to vaporize a portion of streams 416 and 418 before returning them to the reactor. Economizers are explained under "Definitions".

In the present invention, an isobutane vapor stream 402 is produced in the same manner as in the conventional system. However, the quantity of vapor produced may be reduced by 10 to 20% by incorporating an economizer, as will be explained later.

Stream 402, which is stream 20 in FIG. 4, flows to compressor 22 for purposes of increasing pressure to about 32 psia; i.e., a compression ratio of about 2:1. The compressed isobutane vapors 24 from the compressor 22 are mixed with vapors in a stream 26 from an economizer 28 as will be explained hereafter. The combined vapor stream 30 flows to the throat of an eductor 32 for purposes of mixing with an absorbent. While any apparatus may be used for mixing the compressed vapors 30 with the absorbent, an eductor is preferred in that it permits use of excess pressure in the absorbent to further compress the vapors from the compressor 22.

The absorbent provides the motivating force in the eductor 32 and is carried to the eductor by means of the line 34 as shown in FIG. 4. The absorbent will be referred to hereafter also as "lean oil" and, upon mixing with the isobutane vapors from the stream 30 in the eductor 32, decreases in pressure from about, for example, 70 to 75 psia to about 30 to 40 psia. Excellent mixing of the lean oil and the vapors from the compressor is achieved in the eductor, resulting in partial condensation of the vapor stream. The eductor effluent 36 flows to a condenser/cooler 38 where it is cooled such as by means of cooling water to approximately, for example, 100° F. It then flows to an accumulator 40, the lean oil flow rate being maintained so as to obtain total condensation of the vapor stream in the accumulator. With total condensation, the isobutane is absorbed in the lean oil, and the combined stream thus may be referred to as "rich oil."

Accumulator 40 also serves as an acid knockout drum to protect the treaters from excessive acid carryover from the reactor. Recovered acid 438 will be recycled back to the reactor.

Rich oil is withdrawn from accumulator 40 through line 42 by means of a pump 44 and is pumped to a bauxite treater or caustic treater 420 to remove any contaminants. Because total rich oil must be treated rather than reactor effluent, the size of the treating system will be much larger than for other reactor systems. Therefore, stream 42 probably will be treated only in systems using cascade reactors. Clean rich oil 422 then flows to the lean oil/rich oil exchanger 46 as shown in FIG. 4.

Refrigerant condensate 70a (FIG. 4) from the rectifier overhead receiver is combined with isoparaffinic hydrocarbons 424 returning from the depropanizer and flows to economizer 28. In economizer 28, the refrigerant condensate autorefrigerates, creating isobutane vapor stream 26 and liquid stream 74. Liquid stream 74 returns to reactor 400.

EFFLUENT REFRIGERATION

Effluent refrigeration is illustrated and explained in detail in U.S. Pat. No. 4,218,575, Webb, Aug. 19, 1980, in FIG. 3 and column 8, line 40, titled "FIG. 3 Effluent Refrigeration". Therefore, FIG. 3 and this section will address only those areas impacted upon by the present invention.

The contactor reactor 500 illustrated in FIG. 3 is a well-mixed vessel containing a heat-exchange bundle 501. The contactor contents are a liquid emulsion of acid catalyst, isoparaffinic hydrocarbons, and olefin feed. As the reaction takes place, the exothermic heat of reaction is removed simultaneously by the cooling medium inside the tubes. Liquid emulsion 502 is withdrawn and sent to the acid settler 504. This is a horizontal vessel with sufficient holding time to permit complete separation of the liquid hydrocarbon stream 508, containing alkylate and isoparaffinic hydrocarbons, and the acid catalyst 506. Acid catalyst is returned to the contactor 500. Pressure in the settler is maintained at 65 to 90 psia to maintain the hydrocarbon stream in the liquid state. The pressure on stream 508 is reduced to 17 to 25 psia resulting in equilibrium vaporization. The resulting stream of cool vapor and liquid is passed through the tube bundle 501 to remove the heat of reaction. The tube bundle effluent 510 flows to suction trap 512 at, for example, 33° F. and 18.6 psia where the isobutane vapors 516 are separated from the liquid reactor effluent 514. Reactor effluent is then pumped to the deisobutanizer for further processing and recovery of the alkylate product.

Isobutane vapors 516 flow to compressor 518 where pressure is increased to 85 to 135 psia; i.e., a compression ratio of 5 to 9:1. The compressor discharge 520 is cooled and condensed at about 100°–120° F. in exchanger 522 and flows to the refrigerant accumulator 524. A portion of the refrigerant condensate 526 is sent to the depropanizer through line 528 to purge propane from the system. The balance of the condensate is returned through line 530 to the compressor suction trap 512. The bottoms from the depropanizer returns through line 532 to the suction trap as well. In the suction trap 512, the pressure on streams 530 and 532 is reduced to, say, 18.6 psia, resulting in partial vaporization and chilling of the condensate. Approximately 20% of the condensate is vaporized. The suction trap 512 is divided into two sections (by means of a wier 513) which maintain segregation of the liquid condensate from the liquid reactor effluent, but which permits the comingling of the isobutane vapors created by the equilibrium vaporization of both streams. These vapors flow to compressor 518 as a single stream 516. In some larger installation, economizers are used to save compressor horsepower. These were discussed under "Definitions".

In the present invention, the liquid hydrocarbon stream 508 will flow from the acid settler 504 to an acid knockout vessel 540. Here, excessive acid catalyst carryover from settler 504 will be removed to protect the bauxite treaters. Recovered acid 542 will return to the process. The hydrocarbon stream 544 will flow to the bauxite treater 546 where contaminants are removed. After treating, pressure will be reduced on stream 548 and it will flow to the contactor tube bundle 501 to provide refrigeration. It then flows to the suction trap.

Processing around the suction trap will be explained in a detailed discussion of FIG. 4 and the present invention.

CLOSED CYCLE EFFLUENT REACTOR SYSTEM

The closed cycle effluent reactor system utilizes the same well mixed contactor vessel containing a heat-exchanger bundle as the one shown in FIG. 3 (Item 500). The major difference is that a closed cycle refrigeration system employing any refrigerant such as ammonia, propane, etc., is used to remove heat in bundle 501. Reactor effluent 508 from the acid settler is pumped to the deisobutanizer for further processing. This system is illustrated and explained in detail in U.S. Pat. No. 4,218,575, Webb, in FIG. 2 and Column 6, line 24, entitled "FIG. 2".

In the present invention, reactor effluent will be substituted for the refrigerant in bundle 501, converting the existing system into an effluent refrigeration system as shown in FIG. 3. Proposed modifications are the same as for effluent refrigeration.

As discussed under "Time-Tank", this conversion will have the added benefits of increasing isobutane concentration in the reaction zone, thereby improving alkylate quality and yield and decreasing utility consumption on the deisobutanizer.

Referring now to FIG. 4, while not shown in this schematic diagram, it is understood that any conventional reactor system may be used which either creates or is modified to create isobutane vapors. These vapors are represented by streams 16 and 18 in systems utilizing a suction trap such as effluent refrigeration or modified closed cycle effluent reactor systems, or stream 20 from cascade reactor and modified time-tank systems. Since detailed calculations were prepared for an effluent reactor system, this system will be used to illustrate the preferred embodiment. Variations from this explanation required to accommodate different systems have been disclosed in the previous discussion of the individual reactor systems.

The effluent from the alkylation reactor is represented in FIG. 4 by the reference character 10 and is fed to a suction trap 12 where it is flashed at, for example, 33° F. and about 18.6 psia. A chilled liquid frame 14 is withdrawn from the suction trap and contains, for example, alkylate and isoparaffinic hydrocarbons. The liquid stream 14 may be further processed as desired for recovery of the alkylate product as, for example, in a manner as will be explained hereafter in relation to FIG. 5.

In the suction trap 12, vapors comprising predominantly isobutane are flashed and withdrawn in the stream 16 and mixed with a vapor stream 18 to form a composite vapor stream 20. The vapor stream 18 comprises predominantly isobutane vapors generated by the auto-refrigeration of liquid isobutane returning to the suction trap 12 in the stream 74 as will be explained hereafter. Although streams 16 and 18 are shown as separate streams, mechanically they are mixed within the suction trap and a single vapor line 20 leaves the suction trap vessel. The composite isobutane vapor stream 20 flows to the suction of a compressor 22 designated in FIG. 4 with the letter "C" for the compressor and the letter "D" for the driver. While the compressor is not essential to the present process, it is preferred for purposes of increasing pressure of the stream 20 to about 32 psia, i.e., about a 2:1 compression ratio.

The compressed isobutane vapors 24 from the compressor 22 are mixed with vapors in a stream 26 from an economizer 28 as will be explained hereafter. The combined vapor stream 30 flows to the throat of an eductor 32 for purposes of mixing with an absorbent. While any apparatus may be used for mixing the compressed vapors 30 with the absorbent, an eductor is preferred in that it permits use of excess pressure in the absorbent to further compress the vapors from the compressor 22.

The absorbent provides the motivating force in the eductor 32 and is carried to the eductor by means of the line 34 as shown in FIG. 4. The absorbent will be referred to hereafter also as "lean oil" and, upon mixing with the isobutane vapors from the stream 30 in the eductor 32, decreases in pressure from about, for example, 70 to 75 psia to about 30 to 40 psia. Excellent mixing of the lean oil and the vapors from the compressor is achieved in the eductor, resulting in partial condensation of the vapor stream. The eductor effluent 36 flows to a condenser/cooler 38 where it is cooled such as by means of cooling water to approximately, for example, 100° F. It then flows to an accumulator 40, the lean oil flow rate being maintained so as to obtain total condensation of the vapor stream in the accumulator. With total condensation, the isobutane is absorbed in the lean oil, and the combined stream thus may be referred to as "rich oil."

Rich oil is withdrawn from the accumulator 40 through the line 42 by means of a pump 44 and is pumped to a heat exchanger 46. In the exchanger 46, the rich oil is heated by indirect heat exchange with lean oil, i.e., fresh absorbent, flowing to the exchanger 46 in the line 48. The lean oil thus is cooled, exits the exchanger as the stream 50 and joins the line 34 as the motivating force to the eductor 32.

The heated rich oil 52 from the exchanger 46 is passed to a flash drum 54, creating a vapor stream 56 and a liquid stream 58. The vapor stream 56 is fed to the bottom vapor zone of a rectifier or distillation column 60 while the liquid stream 58 is fed to an intermediate tray or level in the rectifier 60.

The rectifier 60 is a reboiled distillation column suitably arranged to separate isobutane (i.e., the refrigerant vapors) from the circulating lean oil. The vapor is separated from the lean oil as it rises through trays or packing in the rectifier 60. The overhead vapor stream 62 comprises predominantly isobutane as distillate and is condensed in a heat exchanger 64 (e.g., water cooled condenser) and flows to an appropriate receiver 66. Pressure in the receiver 66, of course, will be determined by the composition and temperature of the condensed isobutane (refrigerant). A portion of the isobutane condensate is refluxed back to the rectifier by means of the line 68 to aid in the separation between the refrigerant and the heavier components of the lean oil. Some fractionation occurs in the rectifier 60. Condensed distillate that is not refluxed to the rectifier is withdrawn from the receiver such as by means of the flow line 70. Generally, it will be preferred to purge residual propane from the isobutane distillate, and this may be accomplished by conventional means as indicated by the reference character 72 in FIG. 4. The purging of propane is necessary to control the propane content of the system, and the rate of purge typically is dictated by the quantity of propane contained in the alkylation unit feedstock as will be understood by those skilled in the art.

The remainder of the distillate 70 flows through the line 70a and then through a throttle valve 73 to the economizer 28. The economizer 28 is a gas/liquid separator which balances on the discharge 24 of the comparator 22 and operates at the pressure of the discharge. With a pressure reduction of the isobutane stream 70 through the valve 73, a portion of the stream vaporizes, chilling the entire stream. The resulting vapors are withdrawn through the line 26 as previously explained. Chilled liquid from the economizer is withdrawn through the line 74 and flows through a throttle valve 76 and thence to the suction trap 12.

Other types of economizers known to those skilled in the art, such as kettle reboilers, which create isobutane vapors at pressures equal to or above the compressor discharge pressure also may be used in conjunction with the economizer disclosed herein or as a substitute for it.

The suction trap 12 preferably is designed such that it has a first compartment 78 that receives effluent from the reactor and a second compartment 80 that receives the chilled liquid stream 74 from the economizer 28. In the compartment 80, vaporous isobutane formed as a result of pressure reduction of the stream 74 through the valve 76 is withdrawn through the line 18 to be processed as previously explained. A liquid stream predominantly comprised of isobutane is withdrawn from the compartment 80 of the suction trap 12 by means of the flow line 82 to be recycled to the alkylation reactor as both a reactant (in excess) and as a refrigerant or coolant.

Heat to the rectifier 60 is supplied through a reboiler 84. That is, a liquid bottoms portion 86 is withdrawn from the rectifier 60 and is passed in indirect heat exchange through the reboiler or exchanger 84 with a source of heat. From the reboiler 84, the liquid bottoms stream 86 is divided into two portions, one portion being returned through the flow line 88 to the rectifier 60, and the other portion being withdrawn through the line 48. As mentioned previously, the portion of the liquid bottoms from the rectifier 60 passing through the line 48 is the lean oil or absorbent, and this stream is cooled by giving up heat to the rich oil in the line 42 by means of the exchanger 46.

In FIG. 4, the heat source to the reboiler 84 is indicated by the reference character 90 while the spent heat source is indicated by the reference character 92. The source of heat in the line 90 may be waste heat from other refinery processes. Excess low pressure (e.g., 10–25 pounds per square inch gauge) steam is one possible source and is highly desirable because of its excellent condensing and heat transfer properties and because the alkylation unit can continue to operate with regular steam in the event the source of low level heat is shut down or cut back.

The source, quantity and temperature level of the waste heat 90 will dictate the temperature of the bottoms 88 of the rectifier 60. This, in turn, will dictate the composition of the lean oil in the line 48. At a temperature of from about 200° to about 250° F., lean oil in the line 48 will contain significant quantities of lighter components such as isobutane. The lighter components are circulated with the lean oil until an equilibrium level is achieved whereby the absorbed refrigerant is rejected overhead through the line 62 from the rectifier 60. As the temperature difference between the reboiler outlet 48 and the refrigerant accumulator 40 increases, the total lean oil circulation in the system will decrease.

Consumption or loss of lean oil in the system will be small inasmuch as the system as explained herein operates at moderate conditions. The primary potential for loss of lean oil is overhead from the rectifier 60 where lean oil might be recycled back to the alkylation reactor with the isobutane distillate in the overhead stream 62. This illustrates the desirability of the lean oil being compatible with the alkylation system. On the other hand, small quantities of $C_6$ and heavier alkylate are contained in the equilibrium vapors flowing to the compressor 22 from the suction trap 12 such that a small quantity of lean oil will be continuously entering the system. If these heavier hydrocarbons are not recovered overhead in the rectifier, a small quantity of lean oil may have to be withdrawn, either continuously or periodically and returned to the reactor system to purge any excess heavy components from the system.

EXAMPLE

Table I is a table illustrating an example of a material balance for the system of FIG. 4 as explained above. By keying the reference characters on the line bearing the legend "Stream" to FIG. 4, moles per hour of hydrocarbon components in the system are indicated together with examples of total flow, temperature, pressure and volumetric flow rates.

TABLE I

|  | Total Reactor Effluent | Effluent Liquid | Effluent Vapor | Recycle Flash Vapor | Compressor Suction | Economizer Flash Vapor |
|---|---|---|---|---|---|---|
| Stream | 10 | 14 | 16 | 18 | 20 | 26 |
| $C_3$, Mols/Hr. | 386.1 | 73.8 | 312.3 | 118.3 | 430.6 | 268.1 |
| $iC_4$, Mols/Hr. | 4,906.4 | 2,001.6 | 2,904.8 | 375.5 | 3,280.3 | 753.0 |
| $nC_4$, Mols/Hr. | 828.1 | 424.4 | 403.7 | 35.4 | 439.1 | 70.9 |
| $iC_5$, Mols/Hr. | 66.3 | 50.4 | 15.9 | .5 | 16.4 | 1.1 |
| $C_8+$, Mols/Hr. | 695.1 | 687.7 | 7.4 | — | 7.4 | — |
| Total | 6,882.0 | 3,237.9 | 3,644.1 | 529.7 | 4,173.8 | 1,093.1 |
| Lbs./Hr. | 433,325 | 225,271 | 208,054 | 29,136 | 237,190 | 59,787 |
| °F. | 33 | 33 | 33 | 16 | 29 | 49 |
| PSIA | 18.6 | 18.6 | 18.6 | 18.6 | 16 | 35 |
| GPM |  | 744 |  |  |  |  |
| MMSCFD |  |  | 33.146 | 4.825 | 37.971 | 9.956 |

|  | Lean Oil | Rich Oil | Propane Purge | Net Refrigerant Condensate | Economizer Liquid | Recycle Refrigerant |
|---|---|---|---|---|---|---|
| Stream | 34 | 42 | 72 | 70a | 74 | 82 |
| $C_3$, Mols/Hr. | 169.1 | 867.8 | 29.2 | 662.4 | 394.3 | 276.1 |
| $iC_4$, Mols/Hr. | 3,772.8 | 7,806.2 | 170.2 | 3,858.7 | 3,105.7 | 2,732.4 |
| $nC_4$, Mols/Hr. | 666.8 | 1,176.7 | 21.5 | 486.3 | 415.5 | 380.5 |
| $iC_5$, Mols/Hr. | 65.1 | 82.6 | .7 | 16.9 | 15.8 | 15.3 |

TABLE I-continued

| | | | | | | |
|---|---|---|---|---|---|---|
| $C_8+$, Mols/Hr. | 11,993.0 | 12,000.4 | — | — | — | 7.4 |
| Total | 16,666.8 | 21,933.7 | 221.6 | 5,024.4 | 3,931.3 | 3,411.7 |
| Lbs./Hr. | 1,640,000 | 1,940,000 | 12,480 | 282,963 | 223,177 | 195,024 |
| °F. | 110 | 100 | 99 | 99 | 49 | 16 |
| PSIA | 70–75 | 35 | 82 | 82 | 35 | 18.6 |
| GPM | 5,082 | 6,234 | 49 | 1,106 | 816 | 688 |
| MMSCFD | | | | | | |

It should be noted that, in the preceding explanation of the system as illustrated in FIG. 4 and Table I, the compression ratio in relation to flow through the compressor 22 is 2:1 as compared with higher rates in conventional alkylation processes. This significantly reduced compression ratio results in substantial economic benefits. While the compression ratio of 2:1 has been selected as a datum reference for purposes of the exemplar values in Table I, illustrates the outstanding savings to be achieved by the use of the absorption refrigeration techniques according to the present invention. If sufficient waste heat is available at a temperature of about 300° F. for the line 90, or if cooling water is capable of cooling the rich oil (e.g., in the stream 42 of FIG. 4) below 100° F., the compressor 22 may be eliminated completely. In such event, it will be recognized that larger quantities of lean oil will be circulated through the system, and the lean oil will contain less light hydrocarbons. As a result, the rectifier 60 would have to operate at relatively higher temperatures. Thus, there will be an optimum compression ratio specific to any particular installation incorporating the present invention, taking into account pressure at the compressor suction, temperature in the accumulator 40, flow rate of lean oil in the line 34, and temperature and pressure of the bottoms 86 in the rectifier 60.

It will be understood that the eductor 32 described above may be optional and that other methods of mixing isobutane vapors with the absorbent (lean oil) may be used. Indeed, the cost of the eductor must be justified based on the savings generated by recovering motive energy from the lean oil in the line 34. In addition, while FIG. 4 illustrates the lean oil stream 34 flowing directly from the exchanger 46 to the eductor 32, in some instances it may be desirable to add a cooler ahead of the eductor 32 to lower the temperature of the lean oil. This would shift the cooling load away from the condenser/cooler 38 and, in some instances better utilize cooling water.

In some instances, it may be preferable to utilize an exchanger ahead of the flash drum 54 to increase vaporization in such tower. This would also reduce capacity requirements of the reboiler 84.

In some instances, it may be preferable to eliminate the flash drum 54, permitting head rich oil in line 52 to flow directly to the inlet of reboiler 84 or into the bottom of the rectifier 60.

As discussed above, the propane purge 72 removes propane from the liquid stream taken from the receiver 66. However, the equilibrium vapor in the receiver 66 is richer in propane than is the liquid. Consequently, in some instances, it may be more economical to compress a vapor stream from the receiver 66 as a propane purge stream, thereby minimizing the amount of hydrocarbons that must be processed through the depropanizer system 72.

Yet another alternative in the system of FIG. 4, may be the provision of an exchanger located in the vapor line 20 between the suction trap 12 and the compressor 22. Chilled vapors in the line 20 thus could be used to cool the refrigerant contained in the line 70a, reducing the amount of vapor created in economizer 28, perhaps permitting the elimination of the economizer 28 and the vapor stream 26. This alternative might reduce the composite vapor stream 30 by as much as 10%, significantly reducing the lean oil rate and the size of equipment associated therewith. Of course, these advantages might be offset in particular installations by the cost of the additional exchanger and compression penalties resulting from the pressure drop through the alternate exchanger and the higher suction temperature.

Finally, with respect to the system illustrated in FIG. 4 and the example of Table I, horsepower of the compressor 22 is greatly reduced over that of conventional systems primarily for two reasons: (1) the compression ratio is reduced from about 5.7:1 as in conventional processes to about 2.1:1, and (2) the quantity of gas is reduced from 47.8 million standard cubic feet per day to about 38 million standard cubic feet per day due to the economizer. Thus, in this example, horsepower requirements of the compressor 22 are reduced by 65 to 70% or about 3,750 horsepower. Taking into account operating cost of the rich oil pump 44, a net of, for example, 3300 compressor horsepower may be realized. Assuming a cost of five cents per kilowatt hour to power the compressor, the resulting savings may be worth approximately $0.37 per barrel of alkylate or approximately $1,000,000 per year under conditions of the example.

ALTERNATIVE EMBODIMENTS

With reference to FIG. 5 of the drawings, the system illustrated is similar to that of FIG. 4 and similar reference characters are employed except as explained hereafter. The system may be modified such that the liquid stream 14 containing alkylate and isoparaffinic hydrocarbons (isobutane) is processed to make further beneficial use of absorption refrigeration according to the present invention. Thus, the liquid reactor effluent stream 14 is passed to a heat exchanger 100. The liquid stream is heated in the exchanger and then flows to a distillation column 102 wherein alkylate product is withdrawn as a bottoms stream 104, and a predominantly isobutane stream 106 is removed overhead of the column 102. A reflux stream 108 is provided for the distillation column 102 by using a portion of the condensed isobutane from the receiver 66. A reboiler 105 is provided to heat a portion of the bottoms stream 104 for return through the line 107 to the column 102.

Lean oil in the stream 50 is divided as by means of a suitable valve arrangement at 110, a portion of the lean oil being withdrawn through the line 112. Lean oil in the line 112 is passed to an eductor 114 as the motivating stream therein, while the predominantly isobutane overhead stream 106 from the column 102 is passed to the throat of the eductor 114. The resulting rich oil in the line 120 may be cooled such as by a water cooler 122 and then combined as by means of the line 124 with rich oil in the stream 36 flowing to the accumulator 40. As a result, the deisobutanizer column 102 may operate at lower temperatures and consequently lower pressures, improving fractionation and lowering the bottoms temperature, i.e., temperature of the stream 104. A lower bottoms temperature permits use of low pressure (e.g., 25 psig) steam in the line 109 to the reboiler 105. By contrast, conventional processes typically require 150–250 psig steam in the deisobutanizer column reboiler. Thus, if the 25 psig steam for the reboiler 105 is drawn from a source that otherwise would be considered waste, it will be recognized that substantial savings will result.

Referring now to FIG. 6, there is illustrated a general schematic flow diagram of a closed absorption refrigeration system to provide indirect heat exchange, i.e., cooling, to condense and cool isobutane in the alkylation process. Thus, as in the case of FIG. 4, the reactor effluent 10 flows to the suction trap 12 for separation of a vapor stream from a liquid stream. The liquid stream 14 is withdrawn from the suction trap, and vapor streams 16 and 18 are withdrawn and combined as stream 20 for passage to the suction side of the compressor 22 (as previously explained with respect to FIG. 4). The compressed isobutane vapor 24 is then passed to an exchanger 200 whereby the predominantly isobutane stream is cooled. From the exchanger 200, the isobutane stream flows through the line 202 to an accumulator 204 for collection as a liquid. The liquid is withdrawn from the accumulator 204 by means of the line 206 for passage through the throttle valve 76 and thence to the compartment 80 of the suction trap 12 as explained previously with respect to FIG. 4.

Total condensation of the predominantly isobutane vapor stream in the line 24 occurs in the exchanger 200 as a result of indirect heat exchange with a coolant supplied in the line 208. The coolant in the line 208 may be an isobutane stream used in combination with lean oil as previously described herein or other coolants used in conventional absorption refrigeration binaries such as ammonia-water or lithium bromide-water.

As is well known in the art, in the lithium bromide system, water is the refrigerant, providing cooling by vaporizing at very low pressures such as 6 mm Hg absolute (0.117 psia). The water vapor is absorbed and condensed by contacting it with a concentrated solution of lithium bromide. The diluted solution is then pumped to a higher pressure and heated to revaporize the water and reconcentrate the solution. The water vapor is condensed and recycled to the evaporator zone. An example of the lithium bromide-water system is described in "Refrigeration and Air Conditioning" by the Air-Conditioning and Refrigeration Institute, published by Prentice-Hall in 1979, page 138.

The ammonia-water system operates in a somewhat similar manner except that ammonia is the refrigerant and dilute ammonia-water solutions are employed as the absorbent. This system operates at higher pressures of 200–300 psia. Ammonia-water systems are discussed in detail in "Ammonia Absorption Refrigeration in Industrial Processes", Gulf Publishing, 1981, by Marcel Bogart.

The alternative embodiment illustrated in FIG. 6 hereof will be described using the ammonia-water system for exemplary purposes only. Thus, the refrigerant in the line 234 comprises liquid ammonia which, upon passing through the valve 236 and the exchanger 200, becomes substantially vaporous and, after combining with a stream in line 245 (to be explained), flows to an absorber-condenser 210 where the vapor is cooled and condensed. The ammonia then passes through the line 212 to an accumulator 214 conventionally characterized as a strong aqua accumulator. The water-ammonia mixture is withdrawn through the line 216 and, by means of a pump 218, is passed to a strong aqua/weak aqua exchanger 220 whereby the strong aqua stream is heated. The strong aqua stream 222 is then sent to the fractionator 224 wherein ammonia is separated from water. Ammonia vapor is withdrawn through the overhead line 226, cooled in the condenser 228, passes to a receiver 230, and is then divided into a reflux stream 232 (which returns to the fractionator column 224) and the liquid ammonia refrigerant stream 234. The liquid ammonia stream 234 passes through an expansion valve 236, resulting in the refrigerant stream 208 as previously explained.

A reboiler 238 is provided to heat a bottoms stream 240 from the fractionator column 224. The resulting heated stream 242 is returned to the fractionator 224. A portion of the bottoms stream 240 is sent through the line 244 as a weak aqua stream to heat the strong aqua stream flowing through the exchanger 220. The weak aqua stream in the line 245 is then mixed with the ammonia vapor stream in the line 246 from the exchanger 200 for further processing.

Heat in the reboiler 238 preferably is from a low level or waste source as previously explained with respect to the line 90 in FIG. 4. Thus, low pressure stream enters the reboiler 238 in the line 248 and is discharged through the line 250. The low pressure stream in the line 248 thereby provides a source of energy for the absorption refrigeration system to cool the isobutane vapor stream which may be recycled as by means of the line 82 to the alkylation reactor.

The present invention, therefore, is well adapted to carry out the objects and attain the ends and advantages mentioned as well as others inherent therein. While a presently preferred embodiment of the invention has been given for the purpose of disclosure, numerous changes in the details of construction and arrangement of parts and steps of the method will be readily apparent to those skilled in the art and which are encompassed within the spirit of the invention and the scope of the appended claims.

What is claimed is:

1. A process for catalytic alkylation of isoparaffinic hydrocarbons with at least one olefin, comprising the steps of,
   (a) contacting the olefin with a molar excess of an isoparaffinic hydrocarbon in the presence of an acid catalyst in a reactor, the reactor effluent including at least alkylate, acid catalyst, and unreacted isoparaffinic hydrocarbons,
   (b) separating substantially all of the acid catalyst from the reactor effluent,
   (c) subjecting the reactor effluent less than acid catalyst from step (b) to a separation step resulting in a substantially liquid stream containing alkylate and hydrocarbons and a substantially vaporous stream containing isoparaffinic hydrocarbon,
   (d) recovering alkylate product from the substantially liquid stream from step (c),
   (e) admixing the substantially vaporous stream from step (c) with an absorbent and condensing the mixture to substantially a liquid,
   (f) heating and rectifying the condensed liquid from step (e) whereby an isoparaffinic hydrocarbon stream is separated as distillate from the absorbent, and (g) condensing the isoparaffinic hydrocarbon stream from step (f) and returning at least a portion of it ultimately to step (a), and returning the absorbent from step (f) to step (e).

2. The process of claim 1 wherein the substantially vaporous stream from step (c) is compressed to a higher pressure prior to step (e).

3. The process of claim 1 wherein the isoparaffinic hydrocarbons include isobutane.

4. The process of claim 1 wherein the olefin is selected from the group consisting of $C_3$, $C_4$ and $C_5$ olefins and mixtures thereof.

5. The process of claim 1 wherein the acid catalyst is selected from the group consisting of sulfuric acid and hydrofluoric acid.

6. The process of claim 1 wherein the absorbent is a hydrocarbon or a mixture of hydrocarbons having a boiling point in the range of from about 50° to about 430° F. and which is compatible with the alkylation process.

7. The process of claim 1 wherein the absorbent is selected from the group consisting of heavy alkylate, total alkylate, heavy naphtha, gasoline boiling range raffinate and combinations thereof.

8. A process for catalytic alkylation of isobutane with an olefin, comprising the steps of, (a) contacting the olefin with a molar excess of isobutane in the presence of a catalyst in a reactor, the reactor effluent including at least alkylate and isobutane, (b) separating from the reactor effluent (i) a substantially liquid stream containing alkylate and isobutane and (ii) a substantially vaporous stream containing isobutane, (c) admixing the substantially vaporous stream (ii) from step (b) with an absorbent and condensing the mixture to substantially a liquid, (d) distilling the condensed liquid stream from step (c) whereby the substantially vaporous stream from (b)(ii) is revaporized and is separated as distillate from the absorbent, and (e) condensing the isobutane distillate from step (d) and returning at least a portion of it ultimately to step (a).

9. The process of claim 8 wherein the substantially vaporous isobutane stream (ii) from step (b) is compressed to a higher pressure prior to step (c).

10. The process of claim 8 wherein admixing in step (c) is carried out in an eductor.

11. The process of claim 8 wherein the olefin is selected from the group consisting of $C_3$, $C_4$ and $C_5$ olefins and mixtures thereof.

12. The process of claim 8 wherein the absorbent is a hydrocarbon or a mixture of hydrocarbons having a boiling point in the range of from about 50° to about 430° F. and which is compatible with the alkylation process.

13. The process of claim 8 wherein the absorbent is selected from the group consisting of heavy alkylate, total alkylate, heavy naphtha, gasoline boiling range raffinate and combinations thereof.

14. The process of claim 8 wherein the catalyst is an acid.

15. The process of claim 8 wherein the absorbent separated from the isobutane distillate in step (d) is cooled by heat exchange with the liquid condensate from step (c) and then returned to step (c).

16. The process of claim 8 wherein the absorbent separated from the isobutane distillate in step (d) is cooled and then divided into first and second portions, the first portion being returned to step (c).

17. The process of claim 16 wherein, (aa) the substantially liquid stream (i) from step (b) is distilled to separate isobutane as a distillate from alkylate product, and (bb) the isobutane distillate from step (aa) is admixed with the second portion of the absorbent, cooled, and the mixture combined with the liquid condensate from step (c).

18. The process of claim 17 wherein a portion of the isobutane distillate from step (d) is passed as reflux to the distillation step (aa).

19. The process of claim 17 wherein the alkylate is recovered for further processing.

20. The process of claim 17 wherein admixing in step (bb) is carried out in an eductor.

21. The process of claim 17 wherein admixing in step (c) is carried out in an eductor and admixing in step (bb) is carried out in an eductor.

22. A process for catalytic alkylation of isobutane with an olefin, comprising the steps of, (a) contacting the olefin with a molar excess of isobutane in the presence of a catalyst in a reactor, the reactor effluent including at least alkylate and isobutane, (b) separating from the reactor effluent (i) a substantially liquid stream containing alkylate and isobutane and (ii) a substantially vaporous stream containing isobutane, (c) condensing the substantially vaporous isobutane stream (ii) from step (b) by
  (i) compressing the stream to a higher pressure, and then
  (ii) passing said stream in indirect heat exchange with a cooling medium from an absorption refrigeration process, and (d) returning at least a portion of the condensed isobutane stream from step (c) to step (a).

23. The process of claim 22 wherein the cooling medium of step (c)(ii) is isobutane and the absorption refrigeration process is an isobutane-lean oil system.

24. The process of claim 22 wherein the cooling medium of step (c)(ii) is water and the absorption refrigeration process is a lithium bromide-water system.

25. The process of claim 22 wherein the cooling medium of step (c)(ii) is ammonia and the absorption refrigeration process is an ammonia-water system.

26. The process of claim 22 wherein the compression in step (c)(i) is carried out at a ratio of up to about 3:1 based on pressures of the stream after and before compression, respectively.

27. A process for catalytic alkylation of isoparaffinic hydrocarbons with at least one olefin, comprising the steps of, (a) contacting the olefin with a molar excess of isoparaffinic hydrocarbons in the presence of a catalyst in a reactor, the reactor effluent including at least alkylate and isoparaffinic hydrocarbons, (b) separating from the reactor effluent (i) a substantially liquid stream containing alkylate and isoparaffinic hydrocarbons and (ii) a substantially vaporous stream containing isoparaffinic hydrocarbons, (c) condensing the substantially vaporous stream (ii) from step (b) by (i) compressing the stream to a higher pressure, and (ii) admixing the stream with an absorbent and cooling whereby the mixture is substantially reduced to liquid form, (d) distilling the condensed liquid stream from step (c) whereby an isoparaffinic hydrocarbons stream is separated as distillate from the absorbent, and (e) condensing the isoparaffinic hydrocarbons stream from step (d) and returning at least a portion of it ultimately to step (a).

28. The process of claim 27 wherein the compression in step (c)(i) is carried out at a ratio of up to about 3:1 based on pressures of the stream after and before compression, respectively.

29. The process of claim 27 wherein the distillation of step (d) is carried out by use of a low level heat source.

30. The process of claim 27 wherein the isoparaffinic hydrocarbons comprises isobutane.

31. The process of claim 27 wherein the olefin is selected from the group consisting of $C_3$, $C_4$ and $C_5$ olefins and mixtures thereof.

32. The process of claim 27 wherein the catalyst is selected from the group consisting of sulfuric acid and hydrofluoric acid.

33. The process of claim 27 wherein the absorbent is a hydrocarbon or a mixture of hydrocarbons having a boiling point of from 50° up to about 430° F. and which is compatible with the alkylation process.

34. The process of claim 27 wherein the absorbent is selected from the group consisting of heavy alkylate, total alkylate, heavy naphtha, gasoline boiling range raffinate and combinations thereof.

35. The process of claim 27 wherein admixing in step (c)(ii) is carried out in an eductor.

36. The process of claim 27 wherein alkylate product is recovered from the substantially liquid stream (i) from step (b).

37. A process for catalytic alkylation of isobutane with at least one olefin, comprising the steps of, (a) contacting the olefin with a molar excess of isobutane in the presence of an acid catalyst in a reactor, the reactor effluent including at least alkylate and isoparaffinic hydrocarbons, (b) separating from the reactor effluent (i) a substantially liquid stream containing alkylate and isobutane and (ii) a substantially vaporous stream containing isobutane, (c) condensing the substantially vaporous isobutane stream (ii) from step (b) by (i) compressing the stream to a higher pressure, and (ii) admixing the stream with an absorbent in an eductor and cooling whereby the mixture is substantially a liquid, (d) distilling the condensed liquid stream from step (c) using a heat source having a temperature in the range of from about 200° to about 300° F. wherein isobutane is separated as distillate from the absorbent, (e) condensing the isobutane distillate from step (d) and returning at least a portion of it ultimately to step (a), and (f) recovering alkylate product from the substantially liquid stream (i) from step (b).

38. In a process for catalytic alkylation of isobutane with at least one olefin wherein the olefin is contacted with a molar excess of isobutane in the presence of an acid catalyst in a reactor, the reactor effluent including at least alkylate and isoparaffinic hydrocarbons, a substantially liquid stream containing alkylate and isobutane being separated from the reactor effluent, and a substantially vaporous stream containing isobutane being separated from the reactor effluent, the improvement comprising the steps of, (a) compressing the substantially vaporous isobutane stream to a higher pressure and admixing said stream with an absorbent followed by cooling and condensing the mixture to substantially a liquid, (b) distilling the condensed liquid stream from step (a) by use of a relatively low level heat source whereby isobutane is separated as distillate from the absorbent, and (c) condensing the isobutane distillate and returning at least a portion of it ultimately to the reactor.

39. The process of claim 38 wherein the admixing of step (a) is carried out in an eductor.

40. The process of claim 38 wherein the compression in step (a) is carried out at a ratio of up to about 3:1 based on pressures of the stream after and before compression, respectively.

41. The process of claim 38 wherein the olefin is selected from the group consisting of $C_3$, $C_4$ and $C_5$ olefins and mixtures thereof.

42. The process of claim 38 wherein the acid catalyst is selected from the group consisting of sulfuric acid and hydrofluoric acid.

43. The process of claim 38 wherein the absorbent is a hydrocarbon or a mixture of hydrocarbons having a boiling point in the range of from about 50° to about 430° F. and which is compatible with the alkylation process.

44. The process of claim 37 wherein the absorbent is selected from the group consisting of heavy alkylate, total alkylate, heavy naphtha, gasoline boiling range raffinate and combinations thereof.

* * * * *